(12) United States Patent
Akashi et al.

(10) Patent No.: US 7,297,329 B2
(45) Date of Patent: Nov. 20, 2007

(54) MAMMALIAN COMMON LYMPHOID PROGENITOR CELL

(75) Inventors: Koichi Akashi, Chestnut Hill, MA (US); Irving L. Weissman, Redwood City, CA (US); Motonari Kondo, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 88 days.

(21) Appl. No.: 11/093,951

(22) Filed: Mar. 29, 2005

(65) Prior Publication Data

US 2005/0191284 A1 Sep. 1, 2005

Related U.S. Application Data

(62) Division of application No. 08/918,537, filed on Aug. 22, 1997, now Pat. No. 6,908,763.

(51) Int. Cl.
*A01N 65/00* (2006.01)

(52) U.S. Cl. ..................... 424/93.1; 435/325

(58) Field of Classification Search ..................... None
See application file for complete search history.

(56) References Cited

U.S. PATENT DOCUMENTS 5,972,627 A * 10/1999 Galy ........................ 435/7.21
6,555,324 B1 * 4/2003 Olweus et al. ............. 435/7.24

OTHER PUBLICATIONS

Galy, Anne, et al., "Human T,B, Natural Killer, and Dendritic Cells Arise From A Common Bone Marrow Progenitor Cell Subset," *Immunity* (Oct. 1995) vol. 3:459-473.
Kawamoto, Hiroshi, et al., "Direct Evidence For The Commitment Of Hematopoietic Stem Cells To T,B and Myeloid Lineages In Murine Fetal Liver," *International Immunology* (1997) vol. 9, No. 7:1011-1019.
Koguma, Masahito, et al., "Selective Proliferation Of Lymphoid Cells From Lineage- c-Kit+Sca-1+Cells By A Clonal Bone Marrow Stromal Cell Line," *Experimental Hematology* (1998) vol. 26:280-287.
Kondo, Motonari, et al., "Identification Of Clonogenic Common Lymphoid Progenitors In Mouse Bone Marrow," *Cell* (Nov. 28, 1997) vol. 91:661-672.
Matsuzaki, Yumi, et Matsuzaki, Yumi, et al., "Characterization Of c-kit Positive Intrathymic Stem Cells That Are Restricted To Lymphoid Differentiation," *J. Exp. Med.* (Oct. 1993) vol. 178:1283-1292.
Moore, Thomas A., "T-Cell Lineage Commitment And Cytokine Responses Of Thymic Progenitors," *Blood* (Sep. 1, 1995) vol. 86, No. 5:1850-1860.
Orlic, Donald, et al., "Interleukin-7Rα mRNA Expression Increases As Stem Cells Differentiate Into T and B Lymphocyte Progenitors," *Experimental Hematology* (1997) vol. 25:217-222.

Palacios, Ronald, et al., "Developmentally Regulated Cell Surface Expression And Function Of c-Kit Receptor During Lymphocyte Ontogeny In The Embryo And Adult Mice," *Development* (Aug. 1992) vol. 115, No. 4:1133-1147.
Veiby, Ole P., et al.,"Combined Signaling Through Interleukin-7 Receptors And flt3 But Not c-Kit Potently And Selectively Promotes B-Cell Commitment And Differentiation From Uncommitted Murine Bone Marrow Progenitor Cells," *Blood* (Aug. 15, 1996) vol. 88, No. 4:1256-1265.
Veihy, Ole P., et al., "Bidirectional Effect Of Interleukin-10 On Early Murine B-Cell Development: Stimulation Of Flt3-Ligand Plus Interleukin-7-Dependent Generation Of CD19- ProB Cells From Uncommitted Bone Marrow Progenitor Cells And Growth Inhibition Of CD19- ProB Cells," *Blood* (Dec. 1, 1997) vol. 90, No. 11:4321-4331.
Blom, et al., "Prethymic CD34 Progenitors Capable of Developing Into T Cells Are Not Committed to the T Cell Lineage," *The Journal of Immunology* (1997) vol. 158:3571-3577.+
Shortman, et al., "Early T Lymphocyte Progenitors," *Annu. Rev. Immunol.* vol. 14:29-47.
Ikuta, et al., "Lymphocyte Development From Stem Cells," *Annu. Rev. Immunol.* vol. 10:759-783.
Ryan, et al., "Expression of Interleukin-7 Receptor by Lineage-Negative human Bone Marrow Progenitors With Enchanced Lymphoid Proliferative Potential and B-Lineage Differentiation Capacity," *Blood* (1997) vol. 89:929-940.
Palacios, et al., "Bone Marrow Clones Representing an Intermediate Stage of Development Between Hematopoietic Stem Cells and Pro-T-Lymphocyte or Pro-B-Lymphocyte Progenitors," *Blood* (1993) vol. 81:1222-1238.
Goodwin, et al., "Cloning of the Human And Murine Interleukin-7 Receptors: Demonstration of a Soluble Form and Homology to a New Receptor Superfamily," *Cell* (1990) vol. 60:941-951.
Tjonniford, et al., "Lineage Commitment of CD34 Human Hematopoietic Progenitor Cells," *Experimental Hematology* (1996) vol. 24:875-882.
Orkin, Stuart H., "Development of the Hematopoietic System," *Current Opinion in Genetics & Development* (1996) vol. 6:597-602.
Georgopoulos, Et al., "The Role of the Ikaros Gene In Lymphocyte Development and Homeostasis," *Annu. Rev. Immunol.* (1997) vol. 15:155-176.

(Continued)

*Primary Examiner*—Q. Janice Li
(74) *Attorney, Agent, or Firm*—Bozicevic, Field & Francis LLP; Pamela J. Sherwood

(57) ABSTRACT

A substantially enriched mammalian hematopoietic cell subpopulation is provided, which is characterized by progenitor cell activity for lymphoid lineages, but lacking the potential to differentiate into myeloid and erythroid lineages. Methods are provided for the isolation and culture of this common lymphoid progenitor cell (CLP). The cell enrichment methods employ reagents that specifically recognize CDw127 (IL-7 receptor α); CD117 (c-kit) protein, in conjunction with other markers expressed on lineage committed cells. The murine cells are also characterized as expressing low levels of sca-1 (Ly-6E and Ly-6A). The CLPs are predominantly cycling, blast cells. These cells give rise to B cells, T cells and natural killer cells, as evidenced by their growth and differentiation in vitro and in vivo.

4 Claims, 3 Drawing Sheets

OTHER PUBLICATIONS

Singh, Harinder, "Gene Targeting Reveals a Hierarchy of Transcription Factors Regulating Specification of Lymphoid Cell Fates," *Current Opinion in Immunology* (1996) vol. 8:160-165.

Su, Lishan, et al., Hematopoietic Stem Cell-Based Gene Therapy for Acquried Immunodeficiency Syndrome: Efficient Transduction and Expression of RevM10 in Myeloid Cells In Vivo and In Vitro.

Eglitis,Martin, et al., "Transduction of Human Hematopoietic Progenitor Cells With Retroviral Vectors Based on the Gibbon Ape Leukima Virus," *Biochemical and Biophysical Research Communications* (1997) vol. 231:477-480.

Andre, Catherine, et al., "Sequence Analysis of Two Genomic Regions Containing the KIT and the FMS Receptor Tyrosine Kinase Genes," *Genomics* (1997) vol. 39:216-226.

Poeschla,Eric, et al., "Development of HIV Vectors for Anti-HIV Gene Therapy," *Proc. Natl. Acad. Sci. USA* (1996) vol. 93:11395-11399.

* cited by examiner

MAMMALIAN COMMON LYMPHOID PROGENITOR CELL

CROSS-REFERENCE TO GOVERNMENT GRANTS

Research performed in support of this application was supported in part by NCI grant CA42551. The United States government may have rights in any patent issuing on this application.

INTRODUCTION

1. Background

The mammalian immune system plays a vital role in protection from disease, but its effectiveness rests on a fragile balance of power. Excessive or inappropriate responses result in autoimmune disease, while a failure to respond results in immunodeficiency. When such conditions occur, therapeutic intervention may be required. However, it is not easy to successfully manipulate such a complex system.

The mature cells of the immune system, T cells, B cells and natural killer cells, continually differentiate from hematopoietic stem cells, through a series of cell divisions. It is believed that after each cell division the developmental potential of the daughter cells is either maintained or further restricted relative to the parent, never expanded. One therefore observes that pluripotential stem cells give rise to multi-lineage committed progenitor cells, which give rise to specific lineages and finally mature cells. The coordinated changes of cellular properties leading to irreversible restriction of lineage commitment may be due to sequential activation or silencing of various genes.

The phenotype of long-lived pluripotential hematopoietic stem cells has been described. However, the identification of intermediate bipotent or oligopotent progenitors has been difficult, since the evaluation of differentiating potential may be perturbed by a possible failure for the cells to read out detectable differentiation to particular lineages, which may be due to failure in reaching suitable microenvironments in vivo, an insufficient expansion for detection in vivo, or the stochastic nature of lineage commitment, at least in vitro.

One approach to immunologic intervention is the replacement of lymphoid cells through engraftment of allogeneic, autologous or modified autologous cells. It is impractical to engraft mature cells for a variety of reasons. They tend to be short lived and specific for recognition of particular antigens. For T cells, there is a danger of graft vs. host disease resulting from the implanted cells reacting against host tissue.

The use of pluripotential of lineage committed progenitor cells circumvents many of the problems that would arise from the transfer of mature cells. However, such progenitor cells must be separated from other hematopoietic cells. Separation requires identification of the cell and characterization of phenotypic differences that can be utilized in a separation procedure. Cells that are amenable to genetic manipulation are particularly desirable.

2. Relevant Literature

A number of review articles have been published addressing the phenotype of cells in hematopoietic lineages. Overall development of the immune system is discussed in Orkin (1996) *Curr. Opin. Genet. Dev.* 6:597-602. Lymphocyte development from stem cells is reviewed in Ikuta et al. (1992) *Annu. Rev. Immunol.* 10:759-783. Early T cell progenitors are discussed in Shortman and Wu (1996) *Annu. Rev. Immunol.* 14:29-47. The role of transcriptional factors in the regulation of hematopoietic differentiation is discussed in Georgopoulos et al. (1997) *Annu. Rev. Immunol.* 15:155-176; and Singh (1996) *Curr. Opin. Immunol.* 8:160-165.

Characterization of hematopoietic progenitor cells that give rise to lymphocytes may be found in Blom et al. (1997) *J. Immunol.* 158:3571-3577; Galy et al. (1995) *Immunity* 3:459-473; Palacios and Samaridis (1993) *Blood* 81:1222-1238; and Tjonnfjord et al. (1996) *Exp. Hematol.* 24:875-882.

Ryan et al. (1997) *Blood* 89:929-940, describe the expression of interleukin-7 receptor by lineage-negative human bone marrow progenitors with enhanced lymphoid proliferative potential and B-lineage differentiation capacity. The human interleukin 7 (IL-7) receptor nucleotide and amino acid sequence may be accessed at Genbank, M29696; the mouse sequence at M29697. A description of the cloning and characterization of these molecules may be found in Goodwin et al. (1990) *Cell* 60:941-951. The human c-kit nucleotide and amino acid sequence may be accessed at Genbank, U63834, a description of the genomic organization and sequences may be found in Andre et al. (1997) *Genomics* 39:216-226. The mouse homolog may be accessed at Y00864, and is described in Qiu et al. (1988) *EMBO J.* 7:1003-1011. Monoclonal antibodies specific for human and murine CD117 (c-kit) and Cdw127 (IL-7 receptor alpha) proteins are commercially available.

Other markers that are useful in characterizing common lymphoid progenitor cells are accessible as follows: mouse peripheral lymph node-specific homing receptor (MEL-14 antigen), Genbank accession no. M25324; human Leu-8 pan leukocyte antigen (MEL-14 antigen), Genbank accession no. X17519; human sialophorin (CD43), Genbank accession no. J04536; mouse leukosialin (CD 43) gene, Genbank accession no. X17018; human T200 leukocyte common antigen (CD45, LC-A), Genbank accession no. Y00062; mouse CD45 antigen, Genbank accession no. L36091; mouse heat stable antigen, Genbank accession no. X53825.

Examples of methods for the genetic manipulation of hematopoietic stem cells may be found in Su et al. (1997) *Blood* 89: 2283-2290; Eglitis and Schneiderman. (1997) *Biochem Biophys Res Commun* 231:477-480; and Poeschla et al. (1996) *Proc. Natl. Acad. Sci.* 93:11395-11399.

SUMMARY OF THE INVENTION

A substantially enriched mammalian hematopoietic cell subpopulation is provided, which is characterized by progenitor cell activity for lymphoid lineages, but lacking the potential to differentiate into myeloid and erythroid lineages. Methods are provided for the isolation and culture of this common lymphoid progenitor cell (CLP). The cell enrichment methods employ reagents that specifically recognize CDw127 (IL-7 receptor α); CD117 (c-kit) protein, in conjunction with other markers expressed on lineage committed cells. The murine cells are also characterized as expressing low levels of Sca-1 (Ly-6E and Ly-6A). The CLPs are predominantly cycling, blast cells. These cells give rise to B cells, T cells and natural killer cells, as evidenced by their growth and differentiation in vitro and in vivo.

BRIEF DESCRIPTION OF THE DRAWINGS

FIG. 1A is a plot of a FACS analysis of lineage marker (B220, CD4, CD8, CD3, Gr-1 and Mac-1) negative cells subdivided into IL-7Rα positive and negative fractions. Sca-1 and c-Kit profiles of each fraction shows the presence of IL-7Rα$^+$ Sca-1$^{lo}$ c-kit$^{lo}$ cells (upper right) and IL-7Rα$^-$ Sca-1$^{hi}$ c-Kit$^{hi}$ cells (lower right). FIG. 1B is a histogram of the Sca-1, IL-7Rα, and c-kit profiles of the sorted common lymphoid progenitors (filled plot) and hematopoietic stem cells (open solid line); dashed lines show negative staining of whole bone marrow cells.

DESCRIPTION OF THE SPECIFIC EMBODIMENTS

Figure 1:
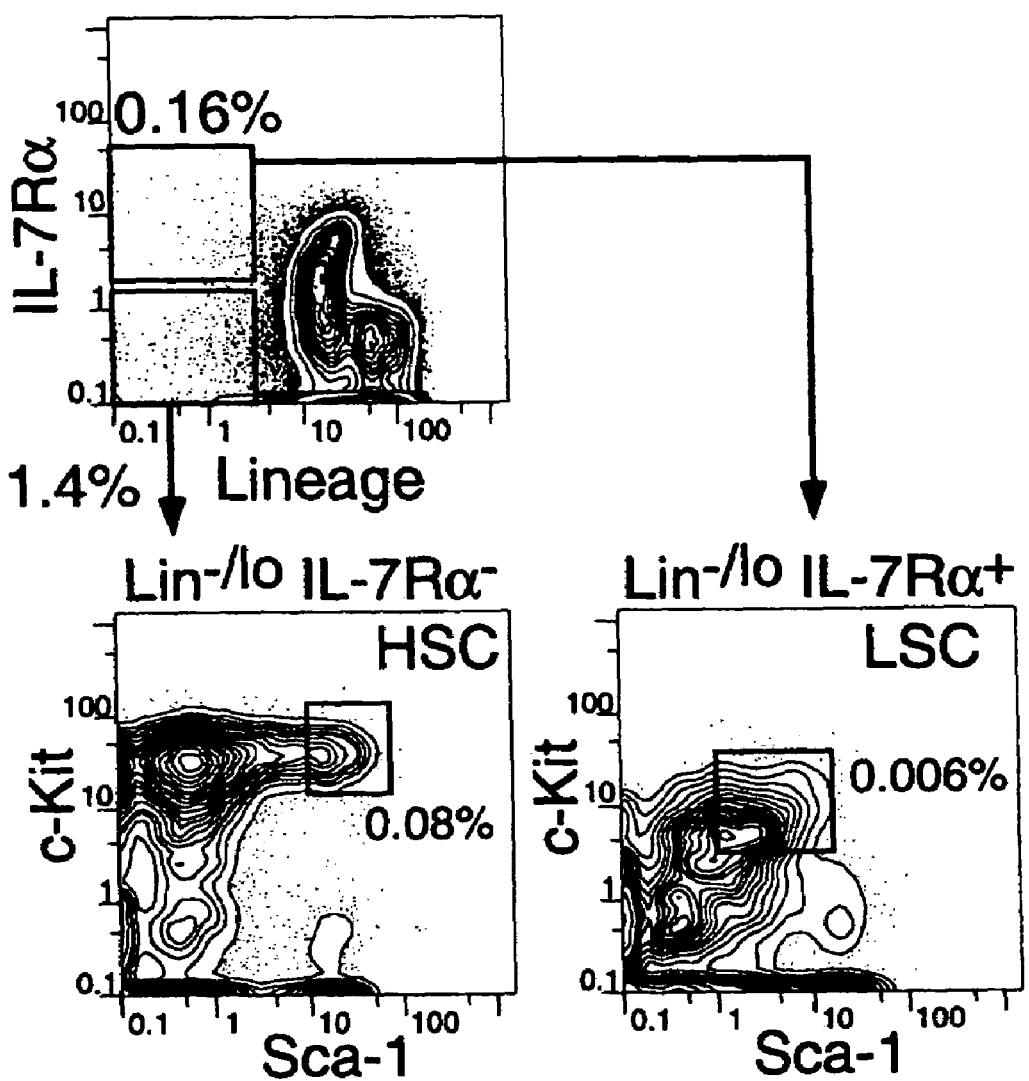
FIGS. 1A and 1B show the identification of IL-7Rα$^+$ common lymphoid progenitors in mouse bone marrow.
Figure 1:
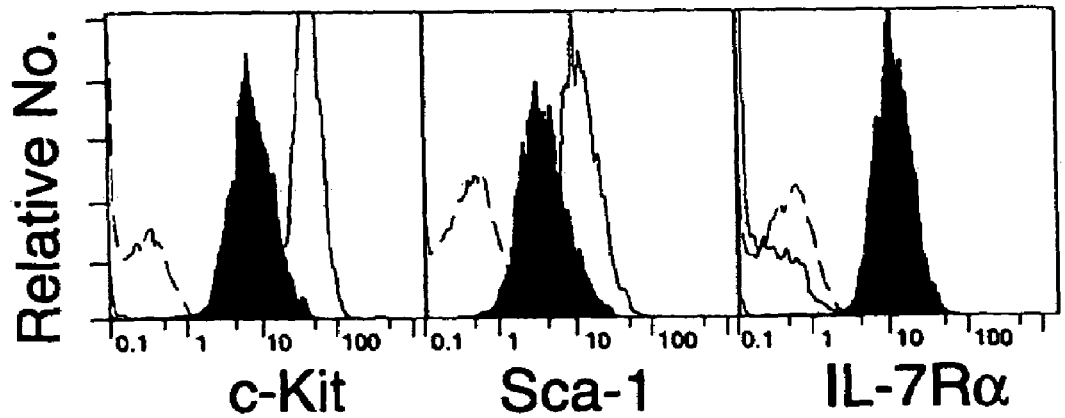

Mammalian hematopoietic progenitor cells that are committed to lymphoid lineages are provided, herein termed a common lymphoid progenitor (CLP). These cells give rise to B cells, T cells and natural killer cells, as evidenced by their growth and differentiation in vitro and in vivo. Unlike the hematopoietic stem cell, the subject cells are developmentally restricted to the lymphoid lineages. The CLP population is useful in transplantation to provide a recipient with lymphoid cells; for drug screening; experimental models of lymphoid differentiation and interaction; screening in vitro assays to define growth and differentiation factors, and to characterize receptors involved in lymphocyte development and regulation; and the like. The native cells may be used for these purposes, or they may be genetically modified to provide altered capabilities.

CLPs are separated from a complex mixture of cells by using reagents that specifically recognize markers on the cell surface, including CDw127 (IL-7 receptor α); CD117 (c-kit) protein, and a cocktail of markers expressed on lineage committed cells. Murine CLP cells are also characterized as expressing low levels of Sca-1 (Ly-6E and Ly-6A). Additional enrichment can be achieved by selection for blast cells.

Methods for enrichment of CLP cells are provided. The enriched cell population will usually have at least about 90% cells of the selected phenotype, more usually at least 95% cells of the selected phenotype. The subject cell populations are separated from other cells, e.g. hematopoietic cells, on the basis of specific markers, which are identified with affinity reagents, e.g. monoclonal antibodies.

CLPs are isolated from any source of hematopoietic progenitor cells, which may be fetal, neonatal, juvenile or adult, including bone marrow, spleen, liver, umbilical cord blood, peripheral blood, mobilized peripheral blood, yolk sac, etc. For autologous or allogeneic transplantation, bone marrow and mobilized peripheral blood are preferred starting materials. For peripheral blood, progenitor cells are mobilized from the marrow compartment into the peripheral bloodstream after treatment with chemotherapy; G-CSF or GM-CSF, or both. A number of single and combination chemotherapeutic agents have been used to mobilize PBPCs. In administering these agents, a balance must be found in all cases between effective PBPC mobilization and possible damage to the hematopoietic stem cell pool and overall patient tolerance. Paclitaxel has been found to effectively mobilize PBPCs without damaging the stem cell pool. A review of peripheral blood stem cells may be found in Shpall et al. (1997) *Annu Rev Med* 48:241-251. As an alternative source of cells, hematopoietic stem cells as described in U.S. Pat. No. 5,061,620, issued on Oct. 29, 1991 may be cultured in vivo or in vitro to provide a source of cells.

The progenitor cells may be obtained from any mammalian species, e.g. equine, bovine, porcine, canine, feline, rodent, e.g. mice, rats, hamster, primate, etc., particularly human. The tissue may be obtained by biopsy or aphoresis from a live donor, or obtained from a dead or dying donor within about 48 hours of death, or freshly frozen tissue, tissue frozen within about 12 hours of death and maintained at below about −20° C., usually at about liquid nitrogen temperature (−180° C.) indefinitely.

The subject CLP cells are characterized by their expression of cell surface markers. For several of these markers, the expression is intermediate in level. While it is commonplace to refer to cells as "positive" or "negative" for a particular marker, actual expression levels are a quantitative trait. The number of molecules on the cell surface can vary by several logs, yet still be characterized as "positive". Characterization of the level of staining permits subtle distinctions between cell populations.

The staining intensity of cells can be monitored by flow cytometry, where lasers detect the quantitative levels of fluorochrome (which is proportional to the amount of cell surface antigen bound by the antibodies). Flow cytometry, or FACS, can also be used to separate cell populations based on the intensity of antibody staining, as well as other parameters such as cell size and light scatter. Although the absolute level of staining may differ with a particular fluorochrome and antibody preparation, the data can be normalized to a control.

In order to normalize the distribution to a control, each cell is recorded as a data point having a particular intensity of staining. These data points may be displayed according to a log scale, where the unit of measure is arbitrary staining intensity. In one example, the brightest cells in a bone marrow sample are designated as 4 logs more intense than the cells having the lowest level of staining, as shown in FIG. 1B. When displayed in this manner, it is clear that the cells falling in the highest log of staining intensity are bright, while those in the lowest intensity are negative. The "low" staining cells, which fall in the 2-3rd log of staining intensity, have properties that are unique from the negative and positive cells. An alternative control may utilize a substrate having a defined density of antigen on its surface, for example a fabricated bead or cell line, which provides the positive control for intensity. The "low" designation indicates that the level of staining is above the brightness of an isotype matched control, but is not as intense as the most brightly staining cells normally found in bone marrow.

The subject CLP cells are characterized by their expression of growth factor receptors. In addition to providing a convenient marker for separation, the cognate ligands are biologically active on CLPs. The subject cells express low levels of c-kit (CD117) on their cell surface. Antibodies that specifically bind c-kit in humans, mice, rats, etc. are known in the art. Alternatively, the c-kit ligand, steel factor (Slf) may be used to identify cells expressing c-kit. The CLP cells express high levels of the IL-7 receptor alpha chain (CDw127). Antibodies that bind to human or to mouse CDw127 are known in the art. Alternatively, the cells are identified by binding of the ligand to the receptor, IL-7.

Murine CLPs express low levels of Sca-1 (Ly-6E and Ly-6A, see van de Rijn (1989) *Proc Natl Acad Sci* 86:4634-4638). Antibodies specific for Sca-1 are known in the art. The expression of high levels of Sca-1 on murine hematopoietic stem cells has been previously described (Spangrude et al. (1988) *J Immunol* 141:3697-3707). A candidate human counterpart for Sca-1 is described in Hill et al. (1996) *Exp Hematol* 24:936-943, as high-level expression of a novel epitope of CD59 identifies a subset of CD34$^+$ bone marrow cells that are highly enriched for pluripotent stem cells.

The CLP subset also has the phenotype of lacking expression of lineage specific markers, exemplified by B220, CD4, CD8, CD3, Gr-1 and Mac-1. For staining purposes a cocktail of binding reagents, herein designated "lin", may be used. The lin panel will comprise binding reagents, e.g. antibodies and functional binding fragments thereof, ligands, peptidomimetics, etc., that recognize two or more of the lineage markers. A lin panel will generally include at least one marker expressed on mature B cells, on mature T cells, on mature granulocytes and on mature macrophages. Markers suitable for use in a lineage panel are typically expressed on these mature cells, but are not present on multiple lineages, or on stem and progenitor cells. The subject cells are characterized as lacking expression of Thy-1, a marker that is characteristic of hematopoietic stem cells. The phenotype of the CLP may be further characterized as Mel-14$^-$, CD43$^{lo}$, HSA$^{lo}$, CD45$^+$ and common cytokine receptor γ chain positive.

The subject CLP population is separated from a complex mixture of cells by techniques that enrich for cells having the above characteristics. For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The subject cells are large, blast cells, therefore an initial separation may select for large cells by various methods known in the art, including elutriation, Ficoll-Hypaque or flow cytometry using the parameters of forward and obtuse scatter to gate for blast cells. A high proportion of the cells are in the mitotic cycle, and vital DNA stains, such as Hoechst 33842 and the like, can be used for separation.

Separation of the subject cell population will then use affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, eg. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (propidium iodide, LDS). Any technique may be employed which is not unduly detrimental to the viability of the selected cells.

The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium which maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The labeled cells are then separated as to the expression of c-kit, IL-7Rα, lin panel, and, for murine cells, Sca-1. The selected population is c-kit low, lin negative, IL-7Rα positive. Optionally the cell population is also selected for low level expression of Sca-1; and by size as described above.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for lymphoid progenitor activity are achieved in this manner. The subject population will be at or about 90% or more of the cell composition, and preferably be at or about 95% or more of the cell composition. The desired cells are identified by their surface phenotype, by the ability to respond to the growth factors Steel Factor, IL-7 and Flk-2 ligand, and being able to provide for development in vivo and in vitro of multiple lymphoid lineages. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. Once thawed, the cells may be expanded by use of growth factors or stromal cells associated with hematopoietic cell proliferation and differentiation.

The enriched cell population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting growth or differentiation of cells, either in culture or in the intact tissue, through specific effects on a transmembrane receptor. Growth factors include polypeptides and non-polypeptide factors. Specific growth factors that may be used in culturing the subject cells include leukemia inhibitory factor (LIF), Flk-2 ligand, oncostatin M; IL-3; IL-6/IL-6 receptor soluble complex; colony stimulating factor-1 (CSF-1), steel factor (c-kit ligand), and IL-7. The specific culture conditions are chosen to achieve a particular purpose, i.e. differentiation into T cell lineage or B cell lineage, maintenance of progenitor cell activity, etc.

In addition to, or instead of growth factors, the subject cells may be grown in a co-culture with stromal or feeder layer cells. Stromal cells suitable for use in the growth of hematopoietic cells are known in the art. These include bone marrow stroma as used in "Whitlock-Witte" (Whitlock et al. [1985] *Annu Rev Immunol* 3:213-235) or "Dexter" culture conditions (Dexter et al. [1977] *J Exp Med* 145:1612-1616); and heterogenous thymic stromal cells (Small and Weissman [1996] *Scand J Immunol* 44:115-121).

The subject cultured cells may be used in a wide variety of ways. The nutrient medium, which is a conditioned medium, may be isolated at various stages and the components analyzed. Separation can be achieved with HPLC, reversed phase-HPLC, gel electrophoresis, isoelectric focusing, dialysis, or other non-degradative techniques, which allow for separation by molecular weight, molecular volume, charge, combinations thereof, or the like. One or more of these techniques may be combined to enrich further for specific fractions.

The progenitor cells may be used in conjunction with the culture system in the isolation and evaluation of factors associated with the differentiation and maturation of lymphoid cells. Thus, the progenitor cells may be used in assays to determine the activity of media, such as conditioned media, evaluate fluids for growth factor activity, involvement with dedication of lineages, or the like.

The subject CLP populations may be used for reconstitution of lymphoid function in an immunocompromised recipient. The condition may be caused by genetic or environmental conditions, e.g. infection with a pathogen such as HIV, exposure to radiation, etc. Conditions having a genetic component include severe or partial combined immunodeficiencies associated with mutations in interleukin receptors, RAG-1, adenosine deaminase and HLA antigen expression; T cell or B cell immunodeficiencies; immunodeficiency with increased IgM due to mutations in the CD40 gene; variable immune deficiency associated with centromeric instability of chromosomes 1, 9, and 16; ataxia-telangiectasia; Wiskott-Aldrich syndrome, associated with mutations in the WAS gene; a gamma globulinemia resulting from defects in Bruton tyrosine kinase; familial histiocytic reticulosis; reticular dysgenesia; Chediak-Higashi-like syndrome; myelodysplasia; etc.

Autologous cells, particularly if removed prior to cytoreductive or other therapy, or allogeneic cells, may be used for progenitor cell isolation and subsequent transplantation.

Genes may be introduced into the CLP cells for a variety of purposes, e.g. prevent HIV infection, replace genes having a loss of function mutation, provide recognition of a particular antigen, suppress activation of a particular antigen receptor, etc. For example, HIV protective forms of the chemokine receptors CCR5, CCR2, and CXCR4 (see Smith et al. (1997) *Science* 277:959-965) can be introduced to provide HIV resistance to the CLP progeny. T cell antigen receptors having a desired recognition (MHC antigen and peptide) can be introduced to provide T cell shaving the desired specificity. Alternatively, vectors are introduced that express antisense mRNA, thereby blocking expression of an undesired gene, e.g. CCR5, CCR2, etc. Other methods of gene therapy are the introduction of drug resistance genes to enable normal progenitor cells to have an advantage and be subject to selective pressure, e.g. the multiple drug resistance gene (MDR).

As the subject cells are largely mitotic, they are particularly good candidates for gene introduction techniques. Various techniques known in the art may be used to transfect the target cells, e.g. electroporation, calcium precipitated DNA, fusion, transfection, lipofection and the like. The particular manner in which the DNA is introduced is not critical to the practice of the invention.

Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. Retrovirus based vectors have been shown to be particularly useful when the target cells are hematopoietic progenitor cells. For example, see Schwarzenberger et al. (1996) Blood 87:472-478; Nolta et al. (1996) P.N.A.S. 93:2414-2419; and Maze et al. (1996) P.N.A.S. 93:206-210.

Combinations of retroviruses and an appropriate packaging line may be used, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) *Mol. Cell. Biol.* 5:431-437); PA317 (Miller et al. (1986) *Mol. Cell. Biol.* 6:2895-2902) GRIP (Danos et al. (1988) *PNAS* 85:6460-6464). Retroviruses packaged with xenotropic envelope protein, e.g. AKR env, are capable of infecting most mammalian cell types, except murine cells.

The sequences at the 5' and 3' termini of the retrovirus are long terminal repeats (LTR). A number of LTR sequences are known in the art and may be used, including the MMLV-LTR; HIV-LTR;AKR-LTR; FIV-LTR;ALV-LTR; etc. Specific sequences may be accessed through public databases. Various modifications of the native LTR sequences are also known. The 5' LTR acts as a strong promoter, driving transcription of the introduced gene after integration into a target cell genome. For some uses, however, it is desirable to have a regulatable promoter driving expression. Where such a promoter is included, the promoter function of the LTR will be inactivated. This is accomplished by a deletion of the U3 region in the 3'LTR, including the enhancer repeats and promoter, that is sufficient to inactivate the promoter function. After integration into a target cell genome, there is a rearrangement of the 5' and 3' LTR, resulting in a transcriptionally defective provirus, termed a "self-inactivating vector".

The vectors may include genes that must later be removed, e.g. using a recombinase system such as Cre/Lox, or the cells that express them destroyed, e.g. by including genes that allow selective toxicity such as herpesvirus TK, bcl-xs, etc.

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in hematopoietic cell types, e.g. IL-2 promoter in T cells, immunoglobulin promoter in B cells, etc.

To prove that one has genetically modified progenitor cells, various techniques may be employed. The genome of the cells may be restricted and used with or without amplification. The polymerase chain reaction; gel electrophoresis; restriction analysis; Southern, Northern, and Western blots; sequencing; or the like, may all be employed. The cells may be grown under various conditions to ensure that the cells are capable of maturation to all of the lymphoid lineages while maintaining the ability to express the introduced DNA. Various tests in vitro and in vivo may be employed to ensure that the pluripotent capability of the cells has been maintained.

The progenitor cells may be administered in any physiologically acceptable medium, normally intravascularly, although they may also be introduced into bone or other convenient site, where the cells may find an appropriate site for regeneration and differentiation. Usually, at least 1×10$^5$ cells will be administered, preferably 1×10$^6$ or more. The cells may be introduced by injection, catheter, or the like. The cells may be frozen at liquid nitrogen temperatures and stored for long periods of time, being capable of use on thawing; If frozen, the cells will usually be stored in a 10% DMSO, 50% FCS, 40% RPMI 1640 medium. Once thawed, the cells may be expanded by use of growth factors and/or stromal cells associated with stem cell proliferation and differentiation.

The subject cells are useful for in vitro assays and screening to detect factors that are active on lymphoid progenitors, particularly those that are specific for lymphoid lineages and do not affect erythroid or myeloid cells. Of particular interest are screening assays for agents that are active on human cells. A wide variety of assays may be used for this purpose, including immunoassays for protein binding; determination of cell growth, differentiation and antigen specificity; production of cytokines, e.g. IL-2; and the like.

The following examples are offered by way of illustration and not by way of limitation.

Experimental

Materials and Methods

Mouse bone marrow cells were stained with unconjugated antibodies for lineage markers (CD3, CD4, CD8, B220, Mac-1, Gr-1 and TER119). Lin$^+$ cells were depleted with sheep anti-rat IgG conjugated immunomagnetic beads (Dynal), and the remaining cells were stained with Texas Red-conjugated anti-rat IgG polyclonal antibodies (Caltag). After incubation with rat IgG (Sigma), cells were stained with FITC-conjugated anti-Sca-1 and APC-conjugated anti-c-kit antibodies. IL-7Rα was stained with biotinylated anti-IL-7Rα antibody and was visualized by PE-conjugated streptavidin (Caltag). The gate for lineage expression in this paper was determined as negative to low, since the fluorescence intensity in the Texas Red channel was not strong enough for separating low and negative expression. Cells were sorted using a highly modified: dual (488-nm argon laser and 599-nm dye laser) or triple laser (plus 390-nm argon laser) FACS (Becton Dickinson) with four-decade logarithmic amplifiers.

Competitive reconstitution was performed by using C57BL/Ka-Thy1.1 mice (Ly5.2) as donors and C57BL/Ka-Thy1.1-Ly5.1 mice as recipients.

For analysis of antigen receptor genes, approximately 2,000 cells of each population were incubated at 94° C. for 10 min in 0.5% Tween D in PCR buffer prior to PCR reaction. Primer sequence used in the 1st PCR were (SEQ ID NO:1) 5'-TAGGCACCTGTGGGGAAGAAAC-3' (Dβ2.1 ext) and (SEQ ID NO:2) 5'-TGAGAGCTGTCTCCTAC-TATC-3' (Jβ2.7 ext). 1/5 aliquots were further amplified with an internal primer pair, (SEQ ID NO:3) 5'-GTATCAC-GATGTAACATTGTG-3' (Dβ2.1 int) and (SEQ ID NO:4) 5'-GGAAGCGAGAGATGTGAATC-3' (Jβ2.7 int). The samples were denatured (94° C., 30 sec), annealed (58° C., 2 min) and extended (72° C., 3 min) for 35 cycles. Amplified DNA was subjected to electrophoresis in 1.2% agarose gel.

Mouse bone marrow cells were stained for the presence of IL-7Rα, c-kit, Sca-1, and a lineage panel. Analysis showed that the majority of cells expressing IL-7Rα were B220$^+$ CD43$^+$ IgM$^-$ pro-B and B220$^+$ CD43$^-$ IgM$^-$ pre-B cells. Among the lineage (Lin)$^-$ cells, the IL-7Rα$^+$ fraction contained a population of Sca-1$^{lo}$c-Kit$^{lo}$ cells that made up ~0.006% of total bone marrow cells; the IL-7Rα$^-$ fraction contained Sca-1$^{hi}$c-kit$^{hi}$ cells, which included the hematopoietic stem cell population, (shown in FIG. 1). The Lin$^-$ IL-7Rα$^+$ Sca-1$^{lo}$ c-Kit$^{lo}$ (CLP) population was mostly negative for Thy-1.1, and they appeared to be blastic (FIG. 3A), suggesting that they were cycling. The immunoglobulin heavy chain and T cell receptor β chain genes were in the germline configuration in these cells.

Figure 2:
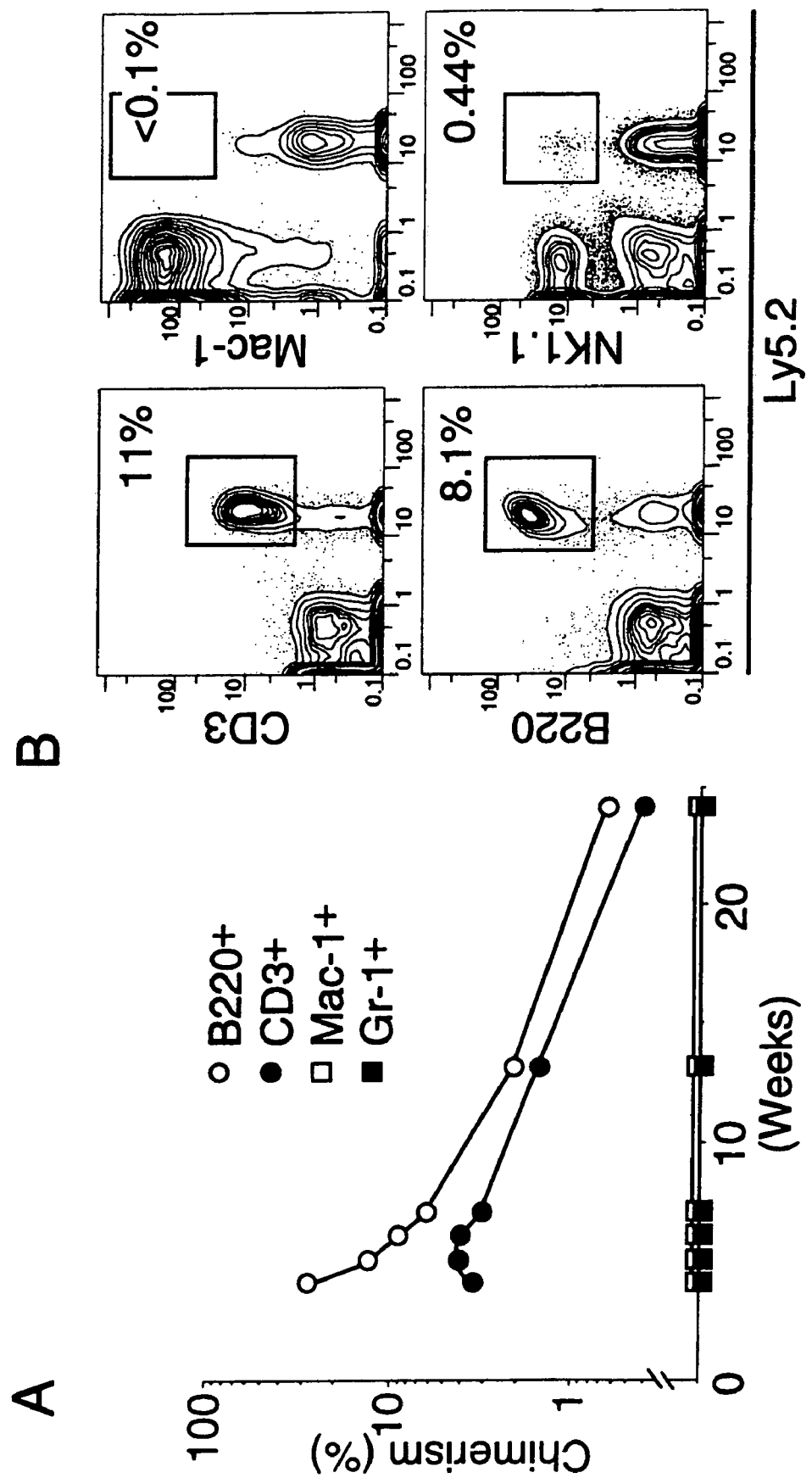
FIGS. 2A and 2B show the reconstitution potential of the Lin$^{-/lo}$IL-7Ra$^+$Sca-1$^{lo}$c-Kit$^{lo}$ population. (2A). Sequential analysis of chimerism after competitive reconstitution. Percentages of donor-derived cells positive for B220 (○), CD3 (●), Mac-1 (□), and Gr-1 (■) are shown. (2B). Intravenous injection of 400 CLPs to sublethally irradiated (600 rad) RAG2$^{-/-}$-Ly5.1 mice. Donor type (Ly5.2) CD3$^+$ and B220$^+$ cells reached 176 cells/μl and 130 cells/μl in blood in this case, respectively, but Mac-1$^+$ cells were absent 4 weeks after injection. Donor-derived NK1.1$^+$ cells could be seen in the spleen 8 weeks after injection in the same mouse.

To examine the differentiation potential of the CLP population, 20 mice were competitively reconstituted with 2,000 congenic CLP cells and 2×10$^5$ syngeneic bone marrow cells. In all 20 mice, there was a rapid reconstitution of donor-derived T and B cells as early as 3 weeks after injection, but not of myeloid (Mac-1 or Gr-1 -positive) cells. The donor-derived T cells had a distribution of Vβ3, Vβ6, Vβ8, and Vβ11 positive cells that was similar to that seen with normal mice. FIG. 2A shows the serial analysis of chimerism in the competitively reconstituted mice. The peak levels of donor type B cells were seen at 4 weeks (the earliest point of analysis) and of T cells at 4 to 6 weeks after injection. The proliferative capacity of the CLP cells was significant; 400 cells could reconstitute 5 to 20% of T and B cells in numbers compared to normal mice 4 weeks after intravenous injection to RAG-2$^{-/-}$ mice (FIG. 2B). However, both donor-derived T and B cells gradually declined (FIG. 2A), indicating that their self-renewal potential is limited. This population also gave rise to NK cells (FIG. 2B).

Figure 3:
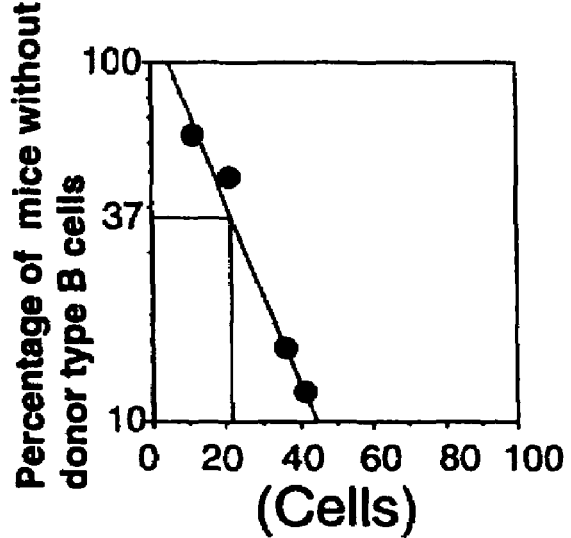
FIGS. 3A, 3B, 3C and 3D show the results of limit dilution analysis of CLP. (3A). B cell reconstitution activity was assessed 4 weeks after intravenous injection of purified Lin$^{-/lo}$IL-7Rα$^+$Sca-1$^{lo}$c-Kit$^{lo}$ CLP population from C57BL/Ka-Thy1.1 (Ly 5.2) mice into lethally irradiated congenic C57BL/Ka-Thy1.1-Ly 5.1 mice. (3B). B220/IgM expression of Ly 5.2 positive cells in a mouse injected with 15 CLP cells. (3C). Thymic colony-formation was assessed 16 days after intrathymic transfer of isolated CLPs (Ly 5.2) into sublethally irradiated (600 rads) congenic (Ly 5.1) mice. (3D). CD4/CD8 profiles of Ly 5.2 positive cells in the thymus of a mouse injected with 10 CLP cells.
Figure 3:
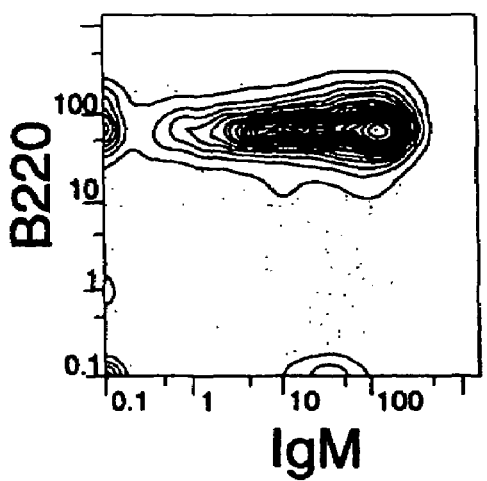
Figure 3:
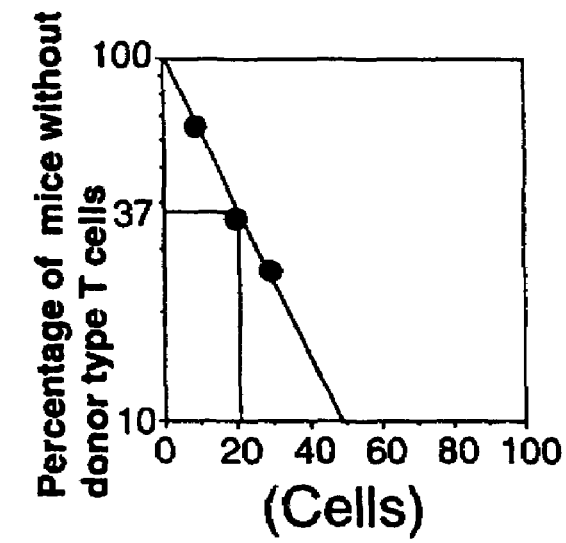
Figure 3:
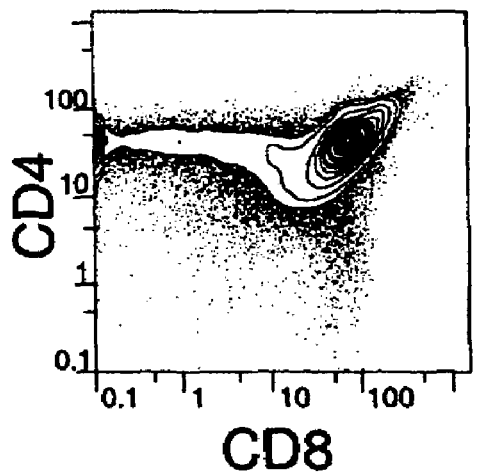

To evaluate rigorously the lymphoid-restricted differentiation capacity of the CLP population, mice were competitively reconstituted with this population at limit dilution, where Poisson statistics predict the mice would be reconstituted by an average of a single cell. As shown in FIG. 3A, the frequency of these cells that can read out B cell differentiation after intravenous injection was approximately 1 in 22 cells (FIG. 3A). The reconstituted B cells were positive for B220 and surface IgM, indicating that they were mature B cells (FIG. 3B). In this experiment, donor-type T cell reconstitution could be detected in only one out of 18 mice that received intravenous injection of 35 CLP cells, possibly due to failure to home to the thymus.

CLP cells were then injected directly into the thymus of sublethally-irradiated congenic mice. Thymocytes derived from the CLP bone marrow cells could be detected 2 weeks after intrathymic injection of as few as 10 cells. By limiting dilution analysis, the frequency of cells with the ability to respond to the thymic microenvironment was approximately 1 in 21 cells (FIG. 3C). CD4 and CD8 profiles of the donor-derived cells showed a normal distribution of CD4 and CD8 single positive (SP) cells, and CD4$^+$CD8$^+$ double positive (DP) cells (FIG. 3D).

Differentiation to the myeloid lineage from CLP cells was undetectable in vivo; 2,000 CLP cells could give rise to neither day 8 CFU-S nor donor-derived myeloid (Mac-1$^+$ or Gr-1$^+$) cells in bone marrow 8 days after injection. To exclude myeloid lineage differentiation potential of the CLP cells more rigorously, the cells were cultured in methylcellulose in the presence of steel factor (Slf), IL-3, IL-6, GM-CSF and erythropoietin. This culture condition allows ~80% of long-term hematopoietic stem cells (HSC) to form a variety of myeloid colonies. As shown in Table 1, no colonies were observed. These in vivo and in vitro data indicate that the CLP cells completely lack myeloid differentiation potential.

TABLE 1

Analysis of CLP and HSC cells for colony-forming potential in methylcellulose in the presence of various cytokines

| | No. of Day 7 Colonies/ 500 cells | | | | | | | |
|---|---|---|---|---|---|---|---|---|
| | Slf + M-CSF | | Slf + IL-3 + IL-6 + GM-CSF + Epo | | Slf + IL-3 + IL-6 + GM-CSF + Epo | | Slf + IL-7 + FL | |
| Cells | M | B | M | B | M | B | M | B |
| CLP* | 0 | 0 | 0 | 0 | 0 | 0 | 0 | 101 |
| HSC† | 1 | 0 | 240 | 0 | 154 | 0 | 2 | 0 |

*cells are Lin$^-$, IL-7Rα$^+$, Sca-1$^{lo}$, Thy-1$^-$, c-kit$^{lo}$.
†cells are Lin$^-$, IL-7Rα$^-$, Sca-1$^{hi}$, Thy-1$^{lo}$, c-kit$^{hi}$.

When the CLP cells were cultured on methylcellulose in the presence of Slf, IL-7 and Flk-2/Flt-3 ligand (FL), 20% of the cells immediately proliferate and form colonies until day 3 (Table 1). All day 3 colonies continued to grow, and became large colonies on day 7. All day 7 colonies analyzed were composed of mainly B220$^+$CD43$^+$IgM$^-$ pro-B cells and some B220$^+$CD43$^-$IgM$^-$ pre-B cells.

To evaluate the bipotential differentiation capacity of a single Lin$^-$, IL-7Rα$^+$, Sca-1$^{lo}$, Thy-1$^-$, c-kit$^{lo}$ cell to T and B cels, a single cell was placed in methylcellulose containing Slf, IL-7 and FL. A part of individual day 3 colonies that contained ~10 to 30 cells were picked, and were injected intrathymically into sublethally irradiated congenic mice. In all cases, residual single cell-derived cells continued to grow in the methylcellulose. These cells were B220$^+$, CD43$^+$, IgM$^-$ pro-B cells and B220$^+$, CD43$^-$, IgM$^-$ pre-B cells by day 14. Two weeks after injection, various numbers of donor-derived T cells could be detected in the injected thymi. In some cases, the injected cells showed normal thymic differentiation for both CD4$^+$ and CD8$^+$ T cells. In the others, the progeny from a single cell consisted of both CD3$^+$ T cells and IgM$^+$, B220$^+$ mature B cells. Therefore, at least some fraction of colony-forming cells in response to Slf, IL-7 and FL retain T lineage as well as B lineage differentiating potential at day 3 of culture.

Based on these data, the subject CLP population has prominent T, B, and NK cell-restricted reconstitution potential, and can give rise to at least both T and B cells. This population may also be able to give rise to dendritic cells, because ~5% of the cells differentiate into morphologically-determined dendritic cells within 5 days on methylcellulose in response to Slf, IL-7, TNF-α plus IL-1β.

The generation of T cells from the CLP population is apparently rapid; the donor-derived T cells reached significant numbers in blood as early as 3 weeks after intravenous injection of the population, when that was undetectable on injection of HSC subsets. Accordingly, it is reasonable to postulate that the CLP population in bone marrow described here could be placed between HSC (IL-7Rα$^-$) subsets and the earliest thymic precursors (IL-7Rα$^+$). The CLPs are likely to acquire IL-7Rα expression (and lose Thy-1 expression) immediately after commitment to lymphoid-restricted differentiation potential.

These studies provide direct evidence for the existence of CLPs in vivo. Further characterization of this population could help clarify events in early lymphoid commitment. The identification of the human CLPs is useful for establishing lymphoid-restricted therapeutic approaches for various immune disorders.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of transplanting lymphoid lineage progenitor cell activity into a mammalian recipient, the method comprising:
    transplanting a substantially pure composition of mammalian common lymphoid progenitor cells, wherein the cells in said composition are characterized as expressing c-kit$^{lo}$, IL-7R$\alpha^+$, lin$^-$, into said recipient;
    wherein said mammalian common lymphoid progenitor cells give rise to T cells, B cells and natural killer cells, wherein an individual c-kit$^{lo}$, IL-7R$\alpha^+$, lin$^-$ progenitor cell in the composition is capable of giving rise to each of T cells, B cells, and natural killer cells, but not to myeloid cells.

2. The method of claim 1, wherein at least 90% of the cells in said composition are characterized as expressing c-kit$^{lo}$, IL-7R$\alpha^+$, lin$^-$.

3. The method of claim 1, wherein at least 95% of the cells in said composition are characterized as expressing c-kit$^{lo}$, IL-7R$\alpha^+$, lin$^-$.

4. A method of transplanting lymphoid lineage progenitor cell activity into a mammalian recipient, the method comprising:
    transplanting a composition having an enriched population of mammalian common lymphoid progenitors into said recipient, wherein said common lymphoid progenitors are characterized as c-kit lo, IL-7R$\alpha$ positive, lin– and give rise to T cells, B cells and NK cells, wherein an individual c-kit$^{lo}$, IL-7R$\alpha^+$, lin$^-$ progenitor cell in the composition is capable of giving rise to each of T cells, B cells, and natural killer cells, but not to myeloid cells.

* * * * *

UNITED STATES PATENT AND TRADEMARK OFFICE
CERTIFICATE OF CORRECTION

PATENT NO. : 7,297,329 B2  
APPLICATION NO. : 11/093951  
DATED : November 20, 2007  
INVENTOR(S) : Akashi et al.

Page 1 of 1

It is certified that error appears in the above-identified patent and that said Letters Patent is hereby corrected as shown below:

In The Specification Under Column 1:

• Please replace lines 4-10 with:

-- FEDERALLY-SPONSORED RESEARCH OR DEVELOPMENT
This invention was made with Government support under contracts CA042551 and AI047458 awarded by the National Institutes of Health. The Government has certain rights in this invention. --

Signed and Sealed this
Twelfth Day of April, 2011

David J. Kappos
*Director of the United States Patent and Trademark Office*

SEQUENCE LISTING

<160> NUMBER OF SEQ ID NOS: 4

<210> SEQ ID NO 1
<211> LENGTH: 22
<212> TYPE: DNA
<213> ORGANISM: M. musculus

<400> SEQUENCE: 1
taggcacctg tggggaagaa ac        22

<210> SEQ ID NO 2
<211> LENGTH: 21
<212> TYPE: DNA
<213> ORGANISM: M. musculus

<400> SEQUENCE: 2
tgagagctgt ctcctactat c        21

<210> SEQ ID NO 3
<211> LENGTH: 21
<212> TYPE: DNA
<213> ORGANISM: M. musculus

<400> SEQUENCE: 3
gtatcacgat gtaacattgt g        21

<210> SEQ ID NO 4
<211> LENGTH: 20
<212> TYPE: DNA
<213> ORGANISM: M. musculus

<400> SEQUENCE: 4
ggaagcgaga gatgtgaatc        20